United States Patent
Gao et al.

(10) Patent No.: US 7,297,502 B2
(45) Date of Patent: Nov. 20, 2007

(54) DEVICES AND METHODS FOR ANALYTE ASSAYS WITH BUILT-IN RESULT REPORTING USING RECOGNIZABLE SYMBOLS

(75) Inventors: Fei Gao, Hangzhou (CN); Shujiang Wu, Hangzhou (CN); Huikang Chen, Hangzhou (CN); DengFeng Xiong, Hangzhou (CN); Jinn-nan Lin, San Diego, CA (US); James McMenamy, San Diego, CA (US)

(73) Assignee: Oakville Hong Kong Company Limited, Central (HK)

( * ) Notice: Subject to any disclaimer, the term of this patent is extended or adjusted under 35 U.S.C. 154(b) by 47 days.

(21) Appl. No.: 11/016,371

(22) Filed: Dec. 17, 2004

(65) Prior Publication Data

US 2006/0134804 A1 Jun. 22, 2006

(51) Int. Cl.
| | |
|---|---|
| *B01L 3/00* | (2006.01) |
| *G01N 15/06* | (2006.01) |
| *G01N 21/77* | (2006.01) |
| *G01N 33/53* | (2006.01) |
| *G01N 33/543* | (2006.01) |
| *G01N 33/558* | (2006.01) |
| *G01N 33/566* | (2006.01) |
| *C12M 1/34* | (2006.01) |
| *C12M 3/00* | (2006.01) |
| *C12Q 1/00* | (2006.01) |

(52) U.S. Cl. .................. 435/7.1; 422/61; 422/68.1; 435/4; 435/287.1; 435/287.2; 435/287.7; 435/287.9; 436/169; 436/501; 436/514; 436/518

(58) Field of Classification Search .................. 422/61, 422/68.1; 435/287.1, 287.2, 287.7, 287.9, 435/4, 7.1; 436/501, 514, 518, 169
See application file for complete search history.

(56) References Cited

U.S. PATENT DOCUMENTS

| | | | |
|---|---|---|---|
| 5,075,078 A | | 12/1991 | Osikowicz |
| 5,160,701 A | * | 11/1992 | Brown et al. .................. 422/56 |
| 6,686,170 B1 | * | 2/2004 | Flanders et al. ........... 435/7.34 |
| 6,855,561 B2 | | 2/2005 | Jerome |
| 2003/0059951 A1 | * | 3/2003 | Frushour et al. ............ 436/510 |
| 2004/0161859 A1 | * | 8/2004 | Guo et al. .................. 436/514 |
| 2006/0029924 A1 | * | 2/2006 | Brewster et al. ............... 435/4 |

FOREIGN PATENT DOCUMENTS

WO 98/22824 * 5/1998

* cited by examiner

*Primary Examiner*—Long V. Le
*Assistant Examiner*—Jacqueline A. DiRamio
(74) *Attorney, Agent, or Firm*—DLA Piper US LLP

(57) ABSTRACT

The present invention provides devices, methods and kits for detecting the presence of an analyte in a liquid sample. The invention provides devices having a positive control area covered with an opaque, movable material, such as an ink, dye, or other material, that is moved on the device by the flow of liquid sample, thereby exposing the positive control area underneath. Using the interaction of colored signals from the positive control area and the analyte binding area, a recognizable symbol is revealed on the device that correlates with the test results, and appears as the test is conducted.

21 Claims, 2 Drawing Sheets

DEVICES AND METHODS FOR ANALYTE ASSAYS WITH BUILT-IN RESULT REPORTING USING RECOGNIZABLE SYMBOLS

FIELD OF THE INVENTION

The present invention is directed to devices for the detection of an analyte and the presentation of test results in as recognizable symbols.

BACKGROUND OF THE INVENTION

The following Background of the Invention is intended to aid the reader in understanding the invention and is not admitted to be prior art.

The inclusion of positive and negative control tests in the performance of an assay is an important component for verifying the validity of the results of any assay. A variety of methods have been used to introduce and include control testing in various assay format. For example, control tests have been included in immunological test formats by utilizing a control zone where analyte is bound to a control line in the assay. Thus, a colored line appears when a labeled control reagent is bound at the control line. These and other types of control tests are effective for verifying that the assay device is functioning correctly, but they also result in added expense and inefficiency in manufacturing the devices and performing the assays, particularly when the specific binding molecules used in the control test are produced as a result of elaborate procedures. Additionally, these types of controls can be confusing for the untrained general consumer and lead to improper test interpretation. There is therefore a need for better and more efficient devices and methods for performing sample testing.

SUMMARY OF THE INVENTION

The present invention provides devices, methods and kits for detecting the presence of an analyte in a liquid sample and indicating to the user the presence or absence of the analyte with recognizable symbols. In one embodiment the present invention provides test strips having a sample application zone, a reagent zone and a detection zone. The detection zone contains a positive control area, a negative control area, and an analyte binding area. The positive control area is delineated by a colored symbol, in this embodiment a minus sign. The analyte binding area is adjacent to and interacts with the positive control area. The analyte binding area contains binding reagents to capture a labeled analyte. In one embodiment, the positive control area or a portion of the detection zone (or the entire detection zone) is covered with an opaque, movable material, for example a dye or ink. At the beginning of the assay, the positive control area is obscured by the opaque, movable material until liquid sample reaches the detection zone. When the liquid sample flows through the detection zone, the opaque, movable material is washed away and the positive control area becomes visible. If no analyte is present in the sample, the revealed positive control area shows the minus sign and the analyte binding area shows no color, indicating a negative result. But if analyte is present in the sample, the labeled analyte binds to the analyte binding area. The positive control area and the analyte binding area interact with each other and produce a plus sign visible to the user. The invention also provides methods of using the devices, and kits containing the devices.

In a first aspect the present invention provides a device for performing an assay to detect the presence or absence of an analyte in a sample. The device has a matrix that supports the flow of a liquid sample, an application zone on the matrix for receiving a liquid sample, and a detection zone on the matrix with a symbol affixed thereto. The detection zone (and the symbol) is at least partially obscured by an opaque, movable material. One or more reagent zones are present on the matrix, containing reagents for conducting the assay. A wide variety of analytes can be tested for using the present invention, for example human chorionic gonadotropin, leutenizing hormone, follicle stimulating hormone, specific and non-specific proteins, blood or blood components, antibodies, drugs and drugs of abuse, urea, nitrite, and glutaraldehyde.

In one embodiment the detection zone contains an analyte binding area and a positive control area. The matrix can be a bibulous material, and the opaque, movable material can be a water soluble ink. For example, the matrix can be a nitrocellulose assay strip and the positive control area is in the shape of a minus sign situated longitudinally on the assay strip. In a related embodiment, the analyte binding area is comprised of two areas situated on either side of the positive control area having a specific binding molecule that binds to the analyte, or to a molecule bound to the analyte. The positive control area and analyte binding area interact to form a recognizable symbol when analyte is present in the sample. In various embodiments the recognizable symbol can be a plus sign, a minus sign, an "X," or another symbol known in the art or in general parlance as conveying a particular meaning. In one embodiment the opaque, movable material is a water soluble ink that covers the positive control area. The specific binding molecule can be an antibody or antibody fragment. In one embodiment the analyte is human chorionic gonadotropin.

In related embodiments the positive control area is delineated by one or more colored zones on the bibulous material and does not comprise a member of a specific binding pair. The analyte can be bound with a label providing a detectable signal, and the label can be a colored particle or a dextran bead. The analyte binding area can be a bar situated latitudinally along the axis of the strip, and can also have a specific binding molecule for the analyte, or for a molecule bound to the analyte.

In another embodiment the label and the positive control area are of the same color. The device can have a sample pad situated at a first end of the device, a detection zone situated near the middle of the test strip, and a label pad situated between the sample pad and detection zone.

Another aspect of the present invention provides for methods of determining the presence or absence of an analyte in a liquid sample using the device of the present invention. The methods involve placing the liquid sample onto the application zone of a device of the invention described herein, allowing the liquid sample to flow through the matrix and thereby pass through the one or more reagent zones so that reagents for conducting the assay react with the liquid sample to form a detectable reaction product when analyte is present in the liquid sample, allowing the liquid sample to flow through the detection zone at least partially obscured by an opaque, movable material, thereby washing away the opaque, movable material to expose a positive control area so that analyte contained in the sample is restrained on the analyte binding area as sample flows through the detection zone, and observing the detection zone of the device to determine the presence or absence of analyte in the liquid sample.

In one embodiment, the liquid sample washes away the soluble ink as liquid sample flows through the detection zone, thereby exposing the positive control area. In a related embodiment the positive control area can be two bars situated on either side of the analyte binding area, and the positive control area and analyte binding area interact to form a recognizable symbol.

In another aspect, the present invention provides kits containing a device of the invention as described herein, and instructions for use of the device. In one kit, the instructions are for use of the device for determining the presence or absence of an analyte in a liquid sample.

The present invention includes a variety of other useful aspects, which are detailed herein. These aspects of the invention can be achieved by using the articles of manufacture and compositions of matter described herein. With reference to the present disclosure, it will be further recognized that various aspects of the present invention can be combined to make desirable embodiments of the invention. In addition, a variety of other aspects and embodiments of the present invention are described herein.

The summary of the invention described above is not limiting and other features and advantages of the invention will be apparent from the following detailed description, as well as from the claims.

DETAILED DESCRIPTION

In the following detailed description, reference is made to the accompanying drawings that form a part hereof, and in which is shown by way of illustration specific embodiments in which the invention may be practiced. It is understood that other embodiments may be utilized and structural changes may be made without departing from the scope of the present invention.

Test Devices

Figure 1:
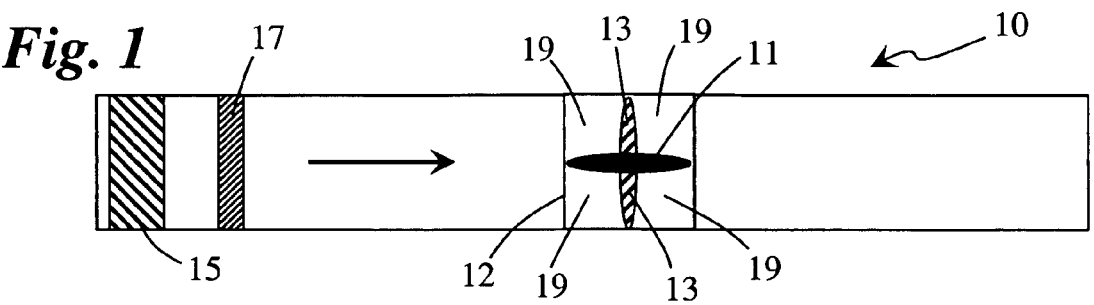
FIG. 1 provides a top view of one embodiment of the device, having a test strip 10, and including an application zone 15, a reagent zone 17, a detection zone 12, a negative control area 19, a positive control area 11, and an analyte detection area 13. The direction of sample flow is illustrated by an arrow.
Figure 2:
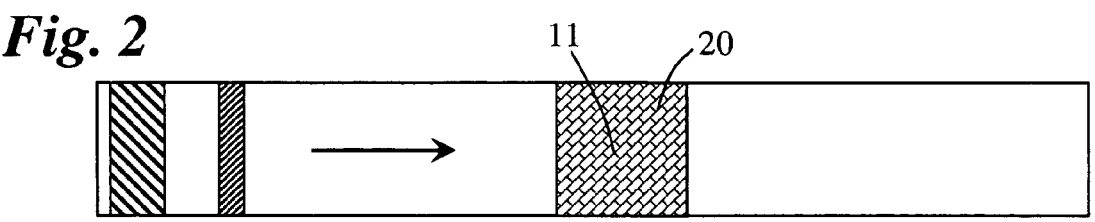
FIG. 2 illustrates one embodiment of the device prior to use, when the entire detection zone is covered by the opaque, movable material 20. The positive control area, is located below the opaque, movable material, which is shown covering the detection zone.
Figure 3:
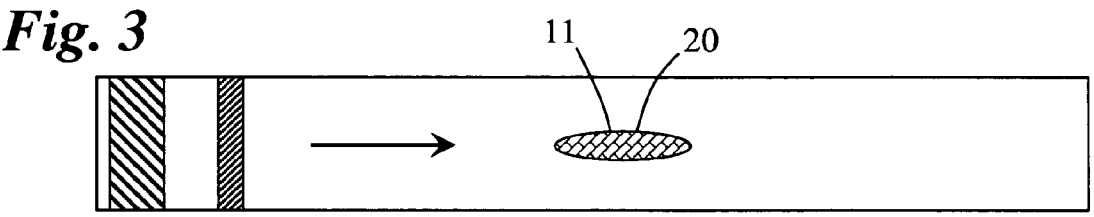
FIG. 3 illustrates another embodiment of the device prior to use, where only the positive control area is covered by the opaque, movable material. The positive control area is located below the opaque, movable material 20, and is shown as a shadow.

The devices of the invention can utilize test strips to detect the presence of an analyte in a liquid sample. The devices use the interaction of colored signals from the positive control area and the analyte binding area to form a recognizable symbol that provides the test result. FIGS. 1-3 illustrate one embodiment of the present device prior to use, a test strip having a matrix that supports the flow of a liquid sample. The device includes an application zone 15 where liquid sample is applied to the device, a reagent zone 17, and a detection zone 12. The reagent zone 17 contains reagents for conducting the assay, and more than one reagent zone can be present on the device depending on the requirements of the particular assay being conducted. The detection zone includes a positive control area 11, an analyte binding area 13 (or test area) and a negative control area 19. The direction of sample flow is indicated in the Figures by an arrow. The sample application zone can contain a buffer for solublizing the sample, or can be simply a location on the matrix for the application of sample, but it also can contain other reagents for conducting the assay. The sample application zone can therefore also be a reagent zone. Sample is advantageously applied in a liquid form to begin the assay, but can also be dried on the test strip and the assay begun by applying water, buffer, or other reagents to solubilize the sample and begin the assay. The sample itself can be a liquid sample, or a solid sample that has been liquefied or otherwise prepared in a liquid form. The reagents contained in the reagent zone can be movably present in the reagent zone. Some reagents can be attached to a label and bind to analytes of interest present in the sample, thereby providing a labeled analyte. The sample application zone and/or reagent zone can also contain buffers for solubilizing the sample or adjusting the pH, as may be required in the specific assay. The test strip is generally a bibulous material providing a matrix to support the flow of liquid. "Matrix" refers to a material that supports the flow and transport of fluid through the device. In one embodiment the matrix is a bibulous material. The flow of fluid through the device can be by force of capillary action. In different embodiments the matrix can be a strip of a single material or may be assembled from more than one bibulous material that are in fluid communication with each other. "Bibulous" materials are those that readily absorb liquid and through which liquid is transported by capillary action.

Examples of bibulous materials include nitrocellulose, filter paper, glass fibers, polyester, and other suitable materials.

Symbols

Recognizable symbols are created by the interaction of the positive control and analyte binding areas on the device. The positive control area can be delineated by choosing a portion of a symbol that will interact with the analyte binding area, and affixing the shape to form the positive control area. The symbol (or portion of a symbol) can be affixed to form the positive control area by methods known in the art, for example by printing or painting the symbol onto the matrix, or by attaching colored particles to a protein and attaching the protein to, within, or underneath the matrix.

In various embodiments the "recognizable symbol" can be a plus sign, a minus sign, a dash, a bar, an "X," or another symbol known in the art or in general as conveying a particular meaning that can be associated with the assay result. Any meaningful symbol can be selected, such as a letter from the Roman alphabet, a number, a mathematical operator, a scientific symbol, or a letter from another language or alphabet system, for example a letter from the Chinese, Japanese, or Arabic alphabets. For example, a minus sign is advantageously used to indicate a negative result, because it is a meaningful and easily recognized symbol, and can also be conveniently configured to interact with an analyte binding area to form a plus sign. Other symbols, such an "X," "O," null sign, "Y," "N," "Z," or an arrow, can also be selected. These symbols can be easily read and understood by an untrained user. When the detectable label and the demarcation of the positive control area are selected to be the same color, the recognizable symbol is formed by the interaction of the positive control area and the analyte binding area when a positive result is obtained. When the symbol is a minus sign, it can have either square or rounded edges.

Positive Control Area

The detection zone of the device contains the positive control area, negative control area, and the analyte binding area. The negative control area is that space located in the detection zone that is not a part of either the positive control area or analyte binding area. If a detectable signal from the detectable label is provided in this area, the assay is invalid due to a failed negative control. In some embodiments the detection zone is a rectangle or square on a bibulous matrix that encompasses the length of the positive control area or analyte binding areas, measuring longitudinally along a test strip, and is further encompassed by lines drawn perpendicular to the sides of the test strip.

The positive control area can be delineated by one or more colored areas on the device and in some embodiments does not contain a member of a specific binding pair. In the embodiment shown in FIG. 4, the positive control area takes the form of a colored symbol affixed to the detection zone, in this case a minus sign situated longitudinally on the assay strip. By "longitudinally" is meant parallel to the direction of sample flow, which generally will be along the length of the matrix. The positive control area may be made by affixing a dye or ink to the matrix, or to a structure underneath the matrix. For example, in those embodiments where a backing is used, the dye, ink, or other material demarcating the positive control area can be affixed on the top or bottom of the backing. The positive control area can also be placed on a structure underneath the test strip, such as situated between the matrix and the housing of the device. The structure can be a piece of plastic or other material with a mark on it. Alternatively, the positive control area can be marked on the housing of the device. Examples of suitable dyes or inks to demarcate the positive control area include, but are not limited to, 3132 fast red 2R, 4230 Malachite blue lake, blue colored latex beads conjugated with BSA, and gold labeled IgG. Of course, many other dyes, inks, or colored materials can also be used and those are not excluded by these examples.

Opaque, Movable Material

In certain embodiments, the opaque, movable material covers only the positive control area (FIG. 3), but in other embodiments it can cover the entire detection zone (FIG. 2), or some portion thereof, or the positive control area and a portion of the detection zone, or a portion of the matrix outside of the detection zone. An "opaque, movable material" is a material that does not transmit an amount of light sufficient to easily view a symbol contained underneath under ordinary room lighting, but which is movable by force of an aqueous solution flowing through or over the matrix. Thus, the symbol contained underneath the opaque, movable material is obscured from view. In some embodiments the symbol is completely obscured, while in others a quantity of light may pass through the material sufficient to discern a faint symbol underneath, but without detrimental effect on interpreting or using the device. Thus, in these embodiments the symbol is not easily viewed, but nevertheless can be discernable.

In the Figures, the positive control area is shown as a shadow. However, in an actual device, the positive control area is obscured from view by the opaque movable material. In one embodiment the opaque, movable material is soluble in an aqueous solution. By "soluble" is meant that an aqueous liquid sample flowing through the detection zone will expose the symbol present underneath the opaque, movable (soluble) material by washing or moving it off of the symbol, such that the symbol is clearly visible to the unaided eye under ordinary room lighting.

When a soluble dye is used as the opaque, movable material, generally any convenient soluble dye can be used, as long as it is sufficiently opaque and is soluble in an aqueous solution. A variety of colored mobilizable dyes can be used. Ponceau 4R and Green coloring matter (Shanghai Dye Institute, Shanghai, China), Rose Red (lot 020811 from Shanghai Marine Painting Materials Company, Shanghai, China), watercolor pigments, and commonly available food colorings all may be used to good effect. In one embodiment the opaque, movable material is a white colored dye. A white titanium oxide ($TiO_2$) food additive can also be used. Thus, when the dye covers and obscures the positive control area, no symbol at all is apparent to the user and the detection zone blends in with the other portions of the matrix. Of course, any color of opaque, movable material can be used, depending on considerations important to the user. The opaque, movable material can be sprayed onto the positive control area, or layered or painted, or applied using any convenient technique. In other embodiments the opaque, movable material can be a particulate substance, such as latex beads or other particular material, as long as the material will be moved off of the positive control area by the flow of fluid.

In one embodiment, the opaque, movable material is selected to be a different color than the positive control area so that when the material is moved off of the positive control area, a symbol of different color than was initially present is apparent and is available to interact with color that may be produced in the analyte binding area.

Analyte Binding Area

The analyte binding area is positioned on the matrix so that it interacts with the positive control area, so that together the two areas provide an apparent detectable symbol when the analyte of interest is present in the liquid sample. Labeled reagents present in a reagent zone can bind to the analyte of interest, thereby labeling the analyte of interest with a detectable label as it flows through the matrix. The analyte binding area also contains reagents that bind to a moiety associated with the analyte. That moiety can be an immunological epitope on the analyte itself, or a reagent bound to the analyte (e.g., from the reagent zone). In various embodiments the reagent bound to the analyte can be an antibody, a fraction or portion of an antibody, an antibody (or fragment thereof) derived from a species different from the antibody affixed to the analyte binding area, or another member of a specific binding pair, for example, avidin, streptavidin, or biotin, which itself can be bound to a moiety bound to the analyte.

The analyte binding area can be a bar situated latitudinally along the axis of the strip, and contain a specific binding molecule for the analyte, or for a molecule bound to the analyte. The analyte binding area can also be two areas on either side of the positive control zone so that when analyte is present in the sample, it is labeled during the assay and is retained at the analyte binding area. The interaction between the color at the analyte binding area and the positive control area provide the recognizable symbol. In some instances the label is a colored particle, which may be a dextran bead, gold sol, or other labeling particle.

Reagent Zone

The label that binds the analyte of interest serves to provide the visually detectable signal in the analyte binding area, which will interact with the positive control area to form the recognizable symbol when analyte is present in the sample. Specific binding molecules for the analyte carrying a label can be present in the reagent zone. When the specific binding molecules capture the analyte, and when the labeled analyte is bound within the analyte binding area, the area becomes visible due to the accumulation of the label in the area. A "specific binding molecule" for the analyte refers to a binding molecule that binds to the analyte and does not substantially bind to any other molecule present in the sample. The specific binding molecule for the analyte can also bind to a molecule that correlates with or indicates the presence of analyte in the sample. By substantial binding is meant that binding occurs to an extent that will affect the result of the assay. In some embodiments the specific binding molecule can be an antibody or an antibody fragment (e.g., the Fab region of an antibody), an antigen, a receptor or fragment of a receptor that binds a ligand, or a member of a biotin-streptavidin pair or other type of binding pair.

A label can thus be provided in the reagent zone, and as the sample flows through the reagent zone the analyte is bound with a label that provides a detectable signal. A "label pad" is an area of the matrix where there is present a label for the analyte suspected of being present in the sample. Therefore, a reagent zone can be a label pad. The "label" can be any suitable label that provides a detectable signal. For example, the label can be a sol particle, a fluorescent molecule, a chemiluminescent molecule, a metal or alloy (e.g. colloidal gold), or a sac, in particular a liposome containing a visible dye. Also useful are hydrophobic sols, which hydrophobic organic dyes or pigments are insoluble in water or soluble only to a very limited extent. The label can also be polymer particles, such as colored polystyrene particles (e.g., spherically shaped). Other useful particulate labels include ferritin, phycoerythrins or other phycobiliproteins, precipitated or insoluble metals or alloys, fungal, algal, or bacterial pigments or derivatives such as bacterial chlorophylls, or other plant materials. In certain embodiments, the label is a colored particle, such as a dextran bead. In other embodiments, the label and the dye used for the positive control are selected to have similar colors, to enhance the interaction of the two signals in producing a single apparent symbol on or in the matrix.

In other embodiments, the label can be a labeled antibody to the analyte. For example, if the analyte of interest is human chorionic gonadotropin (hCG), the label that attaches to the hCG is gold-sol labeled anti-hCG antibody. When the sample reaches the reagent zone (or label pad), the hCG present in the sample is bound by the gold-anti-hCG antibody. The labeled antibody does not interfere with capture antibody present in the analyte binding area, which binds the labeled hCG. The hCG-anti-hCG antibody-gold complex migrates downstream in the matrix. When the complex reaches the analyte binding area the capture antibody, another anti-hCG antibody, binds to another part of the hCG molecule to form a complex of gold-anti-hCG antibody-hCG-anti-hCG antibody. When the gold-anti-hCG antibody-hCG-anti-hCG antibody complex is bound to the analyte binding area, the analyte binding area is colored by the gold label on the complex and therein becomes visible to the unaided eye.

"Antibody" refers to an immunoglobulin, whether natural or partially or wholly synthetically produced. The term also includes derivatives thereof which maintain specific binding ability. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, IgG, and IgE. An "antibody fragment" is any derivative of an antibody which is less than full-length. The antibody fragment can retain at least a significant portion of the full-length antibody's specific binding ability. Examples of antibody fragments include, but are not limited to, Fab, Fab', F(ab')$_2$, scFv, Fv, dsFv diabody, and Fd fragments.

The antibody fragment may be produced by any means. For instance, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

Single-chain Fvs (scFvs) are recombinant antibody fragments consisting of only the variable light chain ($V_L$) and variable heavy chain ($V_H$) covalently connected to one another by a polypeptide linker. Either $V_L$ or $V_H$ may be the NH$_2$-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility. "Diabodies" are dimeric scFvs. The components of diabodies typically have shorter peptide linkers than most scFvs and they show a preference for associating as dimers.

An "Fv" fragment consists of one $V_H$ and one $V_L$ domain held together by noncovalent interactions. The term "dsFv" is used herein to refer to an Fv with an engineered intermolecular disulfide bond to stabilize the $V_H$-$V_L$ pair. A "F(ab')$_2$" fragment is an antibody fragment essentially equivalent to that obtained from immunoglobulins (typically IgG) by digestion with an enzyme pepsin at pH 4.0-4.5. The fragment may be recombinantly produced. A "Fab'" fragment is an antibody fragment essentially equivalent to that obtained by reduction of the disulfide bridge or bridges joining the two heavy chain pieces in the F(ab')$_2$ fragment. The Fab' fragment may be recombinantly produced. A "Fab" fragment is an antibody fragment essentially equivalent to that obtained by digestion of immunoglobulins (typically IgG) with the enzyme papain. The Fab fragment may be recombinantly produced. The heavy chain segment of the Fab fragment is the Fd piece.

The recognizable symbol is formed by the interaction of the positive control area and the analyte binding area. This can be accomplished in several ways, illustrated in FIGS. 6-11. These are intended as non-limiting examples. Symbols of other shapes, such as circles and triangles, are also contemplated.

Figure 4:
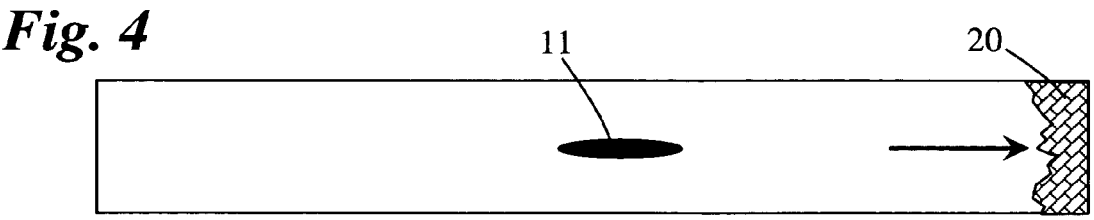
FIG. 4 illustrates the embodiment of FIG. 3 after sample has flowed from the sample application zone to the opposite end of the test strip, when no analyte is present in the applied sample. Note that in this embodiment, the positive control area appears as a minus sign.
Figure 5:
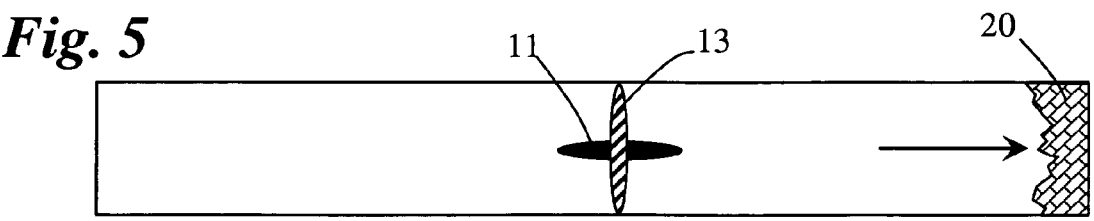
FIG. 5 illustrates the appearance of the device of FIG. 1 after sample has flowed from the application zone to the opposite end of the test strip, when analyte is present in the applied sample. Note that in this embodiment, the positive control area and the analyte detection zone interact to appear as a plus sign.

Prior to use of the device the analyte binding area is not visible to the user. In certain embodiments, the test result will be a plus sign or a minus sign, depending upon the presence or absence of analyte in the sample (FIGS. 4 and 5). FIG. 4 depicts the test results when no analyte is present in the sample. The positive control area has become visible, as a minus sign, since the opaque, movable material has been washed from the detection zone by the movement of liquid sample and migrated to the end of the test strip. FIG. 5 illustrates the test results when analyte is present in the sample; the analyte reacts with the labeled reagent and is captured by the analyte binding area. The analyte binding area is situated latitudinally on the assay strip. By "latitudinal" is meant perpendicular to the direction of fluid flow through the device, which is usually also perpendicular to the length of the test strip. The positive control area and the analyte binding area are situated on the test strip so that they interact with each other and their signals taken together produce a recognizable symbol. In the present example, the symbol is a plus sign. In alternative embodiments, the analyte binding area can be arranged with the positive control area to form other recognizable signs.

Figure 6:
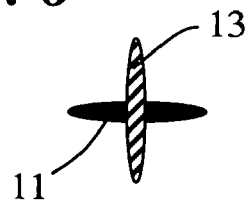
FIG. 6 illustrates one embodiment, in which a plus sign is formed by the interaction of the analyte detection area 13 with the positive control area 11, which overlaps the analyte detection area.

FIG. 6 illustrates one embodiment, in which a plus sign is formed by the analyte detection zone overlapping the positive control area. In this example, the positive control area is laid down longitudinally on the test strip, followed by application of the analyte binding area on top of the positive control area. In different embodiments these areas may or may not overlap. The ink or dye used for the positive control and the analyte label can be selected to be of similar colors, so that the positive control area and the analyte binding area will form a single symbol when they interact. In this case, the positive test symbol is a plus sign. A negative test result produces a minus sign.

Figure 7:
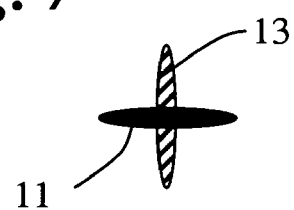
FIG. 7 illustrates a second embodiment, in which a plus sign is formed by the positive control area 11 overlapping the analyte detection zone 13.

FIG. 7 illustrates another embodiment, in which a plus sign is formed by the positive control area and the analyte detection zone, which may or may not overlap. This is similar to the example shown in FIG. 6, except that the analyte binding area is applied to the test strip before the positive control area. Similar to the previous example, a positive test result symbol, with the present arrangement of zones, is a plus sign. A negative test result produces a minus sign.

In another embodiment the positive control can be place laterally on the test strip, and the analyte binding area placed longitudinally. In this orientation, the positive test result symbol would still be a plus sign and a negative test result symbol would be a minus sign.

Figure 8:
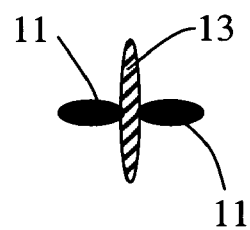
FIG. 8 illustrates another embodiment, in which the positive control area is composed of multiple, aligned bars that are perpendicular to and abut the analyte detection area, and thus appear as a plus sign.
Figure 9:
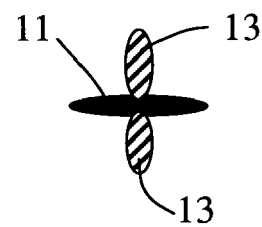
FIG. 9 illustrates an alternative embodiment in which the analyte detection area 13 is composed of multiple, aligned bars that are perpendicular to and abut the positive control area 11, and thus appear as a plus sign.

FIGS. 8 and 9 illustrate alternative methods of making plus signs with the positive control and analyte binding area signals. In the embodiment depicted in FIG. 8, the positive control area is composed of multiple, aligned bars (instead of a single bar) that are perpendicular to and abut the analyte detection zone, and thus form a plus sign. In an alternative embodiment, the analyte binding area is composed of multiple, aligned bars that are perpendicular to and abut the positive control area, which together form a plus sign.

Figure 10:
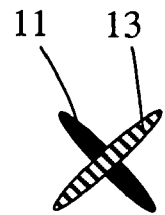
FIG. 10 illustrates another embodiment, in which the analyte detection area 13 and positive control area 11 interact to form an "X." In this situation, the analyte detection and positive control areas are placed at an angle to the direction of sample flow.
Figure 11:
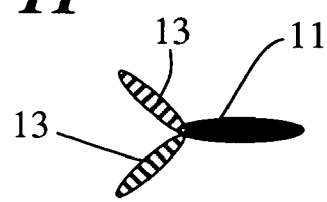
FIG. 11 illustrates a further embodiment, in which the analyte detection area 13 and positive control area 11 interact to form a "Y."

FIG. 10 illustrates another embodiment of the present invention, in which the test and positive control areas interact to form an "X." In this situation, the test and positive control areas are placed at an angle to the direction of sample flow. FIG. 11 illustrates a further embodiment, in which the test and positive control areas interact to for a "Y."

Type of Analytes

The analyte being assayed for presence or absence using the present invention can be any analyte. Examples of analytes that can be readily tested for using the present invention include (but are not limited to) human chorionic gonadotropin (hCG), leutenizing hormone, follicle stimulating hormone (FSH), hepatitis C virus (HCV), hepatitis B virus, hepatitis B surface antigen, HIV, and any drug of abuse. Also, analyte can be detected in any liquid or liquefied sample such as, for example, urine, saliva, oral fluid, blood, plasma, or serum. Additional examples of analytes to be tested for include but are not limited to creatinine, bilirubin, nitrite, protein (nonspecific), blood, leukocytes, sugar, heavy metals or toxins, bacterial components (e.g. protein's or sugars specific to a particular type of bacteria, such as *E. coli*O157:H7, *S. aureus, Salmonella, C. perfringens, Campylobacter, L. monocytogenes, V. parahaemolyticus,* or *B.cereus*). Any other analyte that can be adapted to a lateral flow test format may also be incorporated into the present device.

Types of Samples

Any sample type can be tested with the device of the present invention including liquids of biological origin (e.g., body fluids and clinical samples). Liquid samples may be derived from solid or semi-solid samples, including feces, biological tissue, and food samples. Such solid or semi-solid samples can be converted into a liquid sample by any suitable method, for example by mixing, chopping, macerating, incubating, dissolving or enzymatically digesting solid samples in a suitable liquid (e.g., water, phosphate-buffered saline, or other buffers). "Biological samples" include samples derived from living animals, plants, and food, including for example urine, saliva, blood and blood components, cerebrospinal fluid, vaginal swabs, semen, feces, sweat, exudates, tissue, organs, tumors, tissue and organ culture, cell cultures and conditioned media therefrom, whether from humans or animals. A preferred biological sample is urine. Food samples include samples from processed food components or final products, meat, cheese, wine, milk and drinking water. Plant samples include those derived from any plant, plant tissue, plant cell cultures and conditioned media therefrom. "Environmental samples" are those derived from the environment (e.g., a water sample from a lake or other body of water, effluent samples, soil samples, ground water, ocean water, and runoff water. Sewage and related wastes can also be included as environmental samples.

Methods of Use

The present invention also provides methods of using the devices of the invention to detect the presence or absence of an analyte in a liquid sample. The methods can include the steps of placing a liquid sample onto the application zone of a device of the present invention, and allowing the sample to begin flowing through the test strip. The liquid sample can be placed on the sample application zone by any convenient means, for example by using a dropper.

With reference to FIG. 1, after application of liquid or liquefied sample to the sample application zone 15, the sample begins flow through the matrix and down the test strip. The sample enters a reagent zone 17 where reagents for conducting the assay and/or for labeling the analyte react with the sample. The analyte present in the sample is therefore labeled with a detectable label, in this case an antibody for the analyte carrying a gold sol particle. Of course the label can be any convenient label, for example a gold sol, or an enzyme, or a latex particle. At the beginning of the assay, the detection zone 12 is at least partially obscured by an opaque, movable material, in this case the opaque, movable material covers the positive control area 11. As the sample flows through the detection zone, the movement of the liquid sample washes away the opaque, movable material to expose the positive control area underneath. Also, analyte contained in the fluid sample (and which is now labeled with a detectable label) is restrained on the analyte binding area 13, which contains a member of a specific binding pair for a moiety associated with the analyte, in this case an antibody directed to an epitope directly on the analyte.

The positive control area 11 and the detectable label are selected to have the same color, so that when labeled analyte binds to the analyte binding area 13, the interaction of the positive control area and the analyte control area results in the appearance of a recognizable symbol in the detection zone, in this case a "+" sign.

In cases where no analyte is present in the sample, the primary symbol (the minus sign of the positive control area 11 is apparent in the detection zone, resulting in a minus sign becoming visible after the assay is complete and indicating a negative result for the assay.

Test Kits

The present invention also provides kits containing one or more devices of the present invention, and instructions for use in carrying out an assay. The test kits can be packaged in a variety of formats, depending upon the customer's needs.

In one embodiment, the kits contain devices that are "midstream" fertility test devices, and instructions for using the devices to detect hGH in a urine sample, which indicates a state of pregnancy. The instructions explain how to perform the test and interpret the test results. For example, a woman using the test urinates on the wick, which transfers some of her urine to the test strip. After a few minutes, the opaque, movable material is washed away. If the test is negative (the woman is not pregnant), a minus sign is uncovered when the opaque, movable material washes away. If the test is positive (the woman is pregnant), a plus sign is uncovered when the opaque, movable material washed away, and hCG bound with a detectable label is restrained in the analyte binding area, thereby providing the recognizable symbol.

In another embodiment the kits contain 6, 7, 8, 9, 10, 11, or 12, or more than 3, or more than 4, or more than 5 ovulation test devices and 1, 2, or 3, or more than 1 fertility test devices and instructions. These devices are configured to detect the surge in leutenizing hormone (LH) which precedes ovulation. In this embodiment the instructions relate to use of the test devices in pinpointing the LH surge. In another embodiment the instructions explain female hormonal and ovulation cycles, and how to identify the time of ovulation.

In another embodiment, test strips of the present invention are configured for pregnancy testing in a professional laboratory. The kits include a number of test devices as described above, and optionally include an instruction insert. The kit can contain more than 15 or more than 20 test strips. This type of kit is convenient for use in point of care facilities since it provides a larger number of devices.

EXAMPLE 1

Construction and Testing of Midstream hCG Test Devices

This example describes the construction and use of devices for testing the presence or absence of hCG. This Example uses a green food additive as the opaque, colored material to cover the positive control area. The Example shows that the devices prepared are able to correctly determine the presence of the analyte of interest (hCG) and to provide distinct recognizable symbols for positive and negative test results.

hCG test strips were constructed according to methods known in the art, except where otherwise noted. First, gold sol-labeled goat anti-mouse IgG (1.3 mg/ml, as procedural control line) was applied to a nitrocellulose membrane using a microsyringe controlled by a microprocessor. Mouse anti-ahCG IgG (4.0 mg/ml) was also applied to become the test line, manifested as the analyte binding areas and to form the vertical line of the positive plus sign when hCG is present in the sample. The deposition intensity used was 1.1 µl/cm. Immediately after application, the membrane was dried at 45° C. (2 hours) to immobilize the antibody reagent.

A solution was made by combining apple green food color (1% final concentration; Shanghai Dyestuffs Research Institute, Shanghai, China, lot 99031923) and gold labeled goat anti-mouse IgG (final $OD_{520}$=121) in $Na_2HPO_4$ buffer (50 mM final concentration). This solution was applied to the positive control area on the nitrocellulose membrane, to become the primary recognizable symbol (a "minus" sign) in the detection zone. This symbol present by itself after an assay indicates a negative test result. The solution was applied at a deposition intensity of 0.8 µl/cm. This was done so that a 10 mm line of this solution was striped onto each test strip (to be cut out) from 22 mm to 32 mm from the upstream edge of the test strip. Immediately after application, the membrane was dried overnight at 55° C.

After drying the reagent zone and sample application zone were laminated to the membrane. An absorbent paper was also included to facilitate the movement of fluid through the device. The larger, laminated card was cut into individual test strips of about 60 mm×7.2 mm. The individual test strips were then assembled into midstream test devices, and wicks were also included in the devices. The midstream casing has two windows, one for the test results and one for a procedural control. Prior to use the test window contains a green minus sign and the control window is empty.

1 ml of three urine samples having 0 mIU/ml hCG, 25 mIU/ml hCG, and 100 mIU/ml hCG was applied to three devices in each category, performed in triplicate for a total of 27 devices. A set of three devices in each category would be observed at 3 min, 7 min, and 10 min. As the liquid sample flowed through the matrix, the green dye was washed away from the test window, revealing the red minus sign present underneath as the positive control area. In each of the samples containing 0 mIU/ml of hCG, the red minus sign was present by itself, indicating a negative result in all three time periods.

In those samples containing 25 mIU/ml or 100 mIU/ml of hCG, the hCG present was labeled with an antibody, which was labeled with gold sol, as it flowed through the matrix of the device. When the labeled hCG reached the analyte binding area, it was bound to the area, thereby concentrating the labeled hCG in the analyte binding area, and causing the analyte binding area to appear red in color.

After the assay was complete, the detection zone of the device was observed. In the samples containing 25 mIU/ml of hCG, all of the devices had a red positive control area and a red analyte binding area within 10 min of start of the assay. The positive control area and analyte binding area interacted to appear as a plus sign in the detection zone.

In the devices for the 100 mIU/ml of hCG category, all three devices in each time period showed a plus sign in the detection zone at 3 minutes from start of the assay, thus indicating a positive result for the presence of hCG.

The devices and methods of the invention are useful in a variety of formats. For example, they are useful in a professional laboratory format, such as a point of care facility performing pregnancy tests, or for pinpointing the time of ovulation by identifying the time of the surge of leutenizing hormone. The devices will also be useful in a home testing format for the same purposes. The devices are also useful in contexts apart from fertility testing and can be used to detect the presence of any analyte in any liquid or liquefied sample. The kits described herein are prepared to meet the specific needs of the application of the devices.

The invention illustratively described herein may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The invention claimed is:

1. A device for performing an assay to detect the presence or absence of an analyte in a sample comprising:
   a matrix that supports the flow of a liquid sample;
   an application zone on the matrix for receiving a liquid sample;
   a detection zone on the matrix, wherein the entire detection zone is covered by an opaque, movable material, the detection zone comprising
      an analyte binding area and a positive control area demarcated on the matrix; and
   one or more reagent zones on the matrix comprising reagents for conducting the assay;
   wherein the analyte binding area and positive control area interact to form a recognizable symbol indicative of the presence or absence of analyte in the sample.

2. The device of claim 1 wherein the opaque, movable material is a water soluble ink.

3. The device of claim 1 wherein the matrix is a nitrocellulose assay strip and the positive control area is comprised in the shape of a minus sign situated longitudinally on the assay strip.

4. The device of claim 3 wherein the analyte binding area comprises two areas situated on either side of the positive control area having a specific binding molecule that binds to the analyte, or to a molecule bound to the analyte.

5. The device of claim 1 wherein the positive control area and analyte binding area interact to form a recognizable symbol when analyte is present in the sample.

6. The device of claim 5 wherein the recognizable symbol is a plus sign.

7. The device of claim 4 wherein the opaque, movable material is a water soluble ink that covers the positive control area.

8. The device of claim 4 wherein the specific binding molecule is an antibody or antibody fragment, and the opaque, movable material is a water soluble ink.

9. The device of claim 8 wherein the analyte is human chorionic gonadotropin.

10. The device of claim 4 wherein the positive control area is demarcated by one or more colored zones on the bibulous material and does not comprise a member of a specific binding pair.

11. The device of claim 4 wherein the analyte binding area further comprises a specific binding molecule that specifically binds to the analyte, and comprises a label that provides a detectable signal.

12. The device of claim 11 wherein the label comprises a colored particle.

13. The device of claim 12 wherein the colored particle is a dextran bead.

14. The device of claim 1 wherein the analyte binding area comprises a bar situated latitudinally along the axis of the strip, and further comprises a specific binding molecule for the analyte, or for a molecule bound to the analyte.

15. The device of claim 14 wherein the positive control area comprises two areas situated at either side of the analyte binding area, and the positive control area and analyte binding area interact to form a recognizable symbol.

16. A kit comprising:
   a device for performing an assay to detect the presence or absence of an analyte in a sample comprising:
   a matrix that supports the flow of liquid sample;
   an application zone on the matrix for receiving a liquid sample;

a detection zone on the matrix, wherein the entire detection zone is covered by an opaque, movable material, the detection zone comprising an analyte binding area and a positive control area demarcated on the matrix;

wherein the analyte binding area and positive control area interact to form a recognizable symbol indicative of the presence or absence of analyte in the sample;

one or more reagent zones on the matrix comprising reagents for conducting the assay; and instructions for use of the device.

17. The kit of claim 16 wherein the positive control area is comprised in the shape of a minus sign situated longitudinally on the assay strip, and the opaque, movable material is a water soluble ink.

18. The kit of claim 17 wherein the analyte binding area comprises two areas situated on either side of the positive control area having a specific binding molecule for the analyte or for a molecule bound to the analyte.

19. The kit of claim 18 wherein the recognizable symbol is a plus sign.

20. The kit of claim 17 wherein the specific binding molecule is an antibody or antibody fragment, and the opaque, movable material is a water soluble ink.

21. The kit of claim 18 wherein the analyte is selected from the group consisting of: human chorionic gonadotropin and leutenizing hormone.

* * * * *